United States Patent [19]

Shuto et al.

[11] Patent Number: 5,232,949
[45] Date of Patent: Aug. 3, 1993

[54] 3-(4-SUBSTITUTED-2-CHLOROPHENOXY)-PROPIONALDOXIME ETHYL ETHER COMPOUNDS, THEIR PRODUCTION PROCESSES AND THEIR COMPOSITIONS FOR THE CONTROL OF INSECT PESTS

[75] Inventors: Akira Shuto, Takarazuka; Noriyasu Sakamoto, Nishinomiya; Hirosi Kisida, Takarazuka; Noritada Matsuo, Itami; Hiroaki Fujimoto; Kimitoshi Umeda, both of Toyonaka, all of Japan

[73] Assignee: Sumitomo Chemical Company, Limited, Osaka, Japan

[21] Appl. No.: 879,301

[22] Filed: May 7, 1992

[30] Foreign Application Priority Data

May 20, 1991 [JP] Japan ................ 3-145522

[51] Int. Cl.$^5$ .................. A01N 33/24; C07C 251/38
[52] U.S. Cl. .................... 514/640; 564/256
[58] Field of Search ........... 564/256; 514/640; 71/3

[56] References Cited

U.S. PATENT DOCUMENTS 4,766,152  8/1988  Karrer ................ 564/256

FOREIGN PATENT DOCUMENTS 0164702   9/1984  Japan ................ 514/640
60-56948   4/1985  Japan .
60-246361 12/1985  Japan .
61-260054 11/1986  Japan .
62-252756 11/1987  Japan .
63-203657  8/1988  Japan .

OTHER PUBLICATIONS

Niwa et al. "Development of (phenoxyphenoxy)- and (benzyloxy) alkanaldoxime o-ethers, etc" *J. Agric. Food Chem.* 36 (2) 378-84.
Abst. in *Chem. Abst* Columbus, OH 108(15):126644e.
Chem. Abs., vol. 109, No. 19, 7 Nov. 1988, "Phenoxylakanal Oximes, Their Production . . . ".

*Primary Examiner*—Richard L. Raymond
*Assistant Examiner*—Peter G. O'Sullivan
*Attorney, Agent, or Firm*—Birch, Stewart, Kolasch & Birch

[57] ABSTRACT

A 3-(4-substituted-2-chlorophenoxy)propionaldoxime ethyl ether compound of the formula:

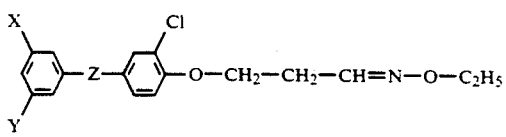

wherein X and Y are, the same or different, a hydrogen atom or a fluorine atom; Z is an oxygen atom or a methylene group in the proviso that X and Y are not a hydrogen atom at the same time when Z is an oxygen atom, which is useful for control of insect pests.

8 Claims, No Drawings

3-(4-SUBSTITUTED-2-CHLOROPHENOXY)PROPIONALDOXIME ETHYL ETHER COMPOUNDS, THEIR PRODUCTION PROCESSES AND THEIR COMPOSITIONS FOR THE CONTROL OF INSECT PESTS

BACKGROUND OF THE INVENTION

1. Field of the Invention

The present invention relates to 3-(4-substituted-2-chlorophenoxy)propionaldoxime ethyl ether compounds, their production processes and their compositions for the control of insect pests.

2. Description of the Prior Art

It is described in Japan Patent Application (laid-open) No. 60-56948, U.S. Pat. No. 4,766,152 that certain oxime ether compounds are useful as insecticides and acaricides. But, their insecticidal and acaricidal activities are still not satisfactory.

OBJECTS OF THE INVENTION

The main object of the present invention is to provide novel oxime ether compounds having improved insecticidal and acaricidal activities.

This object as well as other objects and advantages of the present invention will become apparent to those skilled in the art from the following description.

SUMMARY OF THE INVENTION

As a result of the extensive study seeking oxime compounds producing a satisfactory controlling effect on insect pests, it has been found that those of the following formula exhibit a remarkable juvenile hormone-like activity and can control significantly the growth of insect pests:

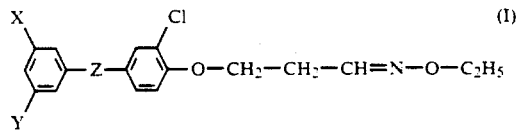

wherein X and Y are, the same or different, a hydrogen atom or a fluorine atom; Z is an oxygen atom or a methylene group in the proviso that X and Y are not a hydrogen atom at the same time when Z is an oxygen atom. The present invention is based on the above finding.

DETAILED DESCRIPTION OF THE INVENTION

The compounds of the above formula (I), i.e. 3-(4-substituted-2-chlorophenoxy)propionaldoxime ethyl ether compounds (I) of the present invention have an excellent juvenile hormone-like activity against insect pests. They exhibit various actions such as metamorphosis inhibition, embryogenesis inhibition and sterilization and are thus efficacious as growth regulators, chemosterilants, ovicides or reproduction inhibitory agents on various insect pests such as agricultural, forestal, hygienic and stored grain insect pests. They are also efficacious against insect pests having an increased resistance to commercial insecticides.

The 3-(4-substituted-2-chlorophenoxy)propionaldoxime ethyl ether compounds (I) of the present invention can be produced by various processes, among which typical examples are shown below.

Process A

The 3-(4-substituted-2-chlorophenoxy)propionaldoxime ethyl ether compound (I) is produced by reacting an aldehyde compound of the formula:

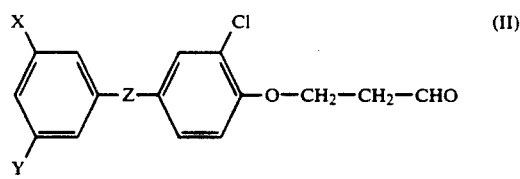

wherein X, Y and Z are each as defined above, with ethoxyamine.

The reaction is ordinarily carried out with or without an inert solvent and in the absence or presence of an acid or alkali at a temperature of from about −30° C. to the boiling point of the reaction mixture, preferably from about room temperature to about 100° C., for from about 0.5 hour to about 24 hours.

The molar proportion of the aldehyde compound (II) and ethoxyamine to be used for the reaction is ordinary to be from 1 : 1 to 1 : 20, preferred to be from 1 : 1.1 to 1 : 1.2.

In the above reaction, the aldehyde compound (II) can be employed in a reactive derivative such as its acetal form, hemiacetal form and hydrate form, etc. Ehtylamine can be also employed in a salt form such as its hydrochloride and sulfate, etc.

Examples of the inert solvent are water, methanol, ethanol, benzene, toluene, pyridine, carbon tetrachloride, chloroform, ethylene chloride, methylene chloride and mixtures thereof. Examples of the acid are hydrochloric acid, sulfuric acid and p-toluenesulfonic acid, etc. Examples of the alikali are an inorganic base (e.g. sodium hydroxide, potassium hydroxide, potassium carbonate, etc.) and an organic base (e.g. triethylamine, pyridine, etc.).

Process B

The 3-(4-substituted-2-chlorophenoxy)propionaldoxime ethyl ether compound (I) is produced by reacting an aldoxime compound of the formula:

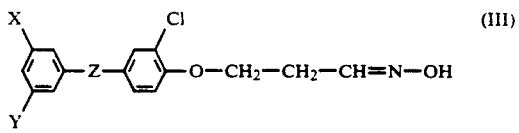

wherein X, Y and Z are each as defined above, with a compound of the formula:

wherein A is a halogen atom, a mesyloxy group and a tosyloxy group.

The reaction is ordinarily carried out with an inert solvent in the presence of an acid bonding agent at a temperature of from −30° C. to the boiling point of the reaction mixture, preferaly from about room temperature to about 100° C., for from about 0.5 hour to about 24 hours.

The molar proportion of the aldoxime (III) and the compound (IV) to be used for the reaction is ordinary to be from 1 : 1 to 1 : 10, preferred to be from 1 : 1.1 to 1 : 1.2.

Examples of the inert solvent are methanol, ethanol, N,N-dimethylformamide, dimethylsulfoxide, tetrahydrofuran, dimethoxyethane, toluene, water, etc. and mixtures thereof. When the inert solvent is water or two layer mixtures of water and an organic solvent(s), an ammonium salt such as triethylbenzylammonium chloride and tetrabutylammonium bromide may be added to the reaction system as a catalyst.

Examples of the acid bonding agent are an alkali metal (e.g. sodium, potassium, etc.), an alkali metal hydride (e.g. sodium hydride, etc.), an alkali metal amide (e.g. sodium amide, etc.), an alkali metal hydroxide (e.g. sodium hydroxide, potassium hydroxide, etc.), an alkali metal carbonate (e.g. sodium carbonate, potassium carbonate, etc.) and an organic base (e.g. triethylamine, trimethylamine, pyridine, etc.).

The above acid bonding agent itself may be added to the reaction system with the other reaction agents. When the acid bonding agent is an acid bonding agent derived from an alkali metal, it can be employed in a salt form having the formula:

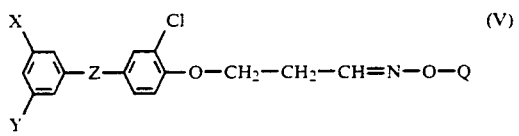

wherein Q is an alkali metal atom and X, Y and Z are each as defined above which is produced by reacting the aldoxime compound with the acid bonding agent.

After completion of the reaction, post-treatment may follow in a per se conventional manner such as extraction with an organic solvent and concentration. When necessary or desired, the product may further be purified by chromatography, distillatron, recrystallization, etc.

The 3-(4-substituted-2-chlorophenoxy)propionaldoxime ethyl ether compounds (I) of the present invention have an oxime structure and can form geometrical isomers. Those geometrical isomers and their mixtures which have biological activities against insect pests fall within the scope of the present invention.

Among the starting compounds in the above processes, the aldehyde compound (II) is produced from an acetal compound having the formula:

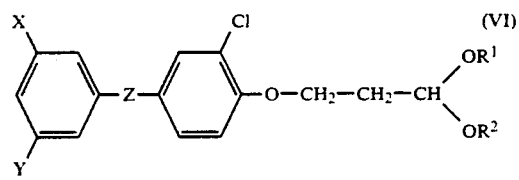

wherein X, Y and Z are each as defined above and $R^1$ and $R^2$ are, the same or different, an $C_1$-$C_4$ alkyl group and may be conbined together to represent a saturated five or six membered ring by the known method as described in J. Chem. Soc., 3864 (1953); Synth. Commun., 7, 409 (1977); etc.

Furthermore, the acetal compound (VI) is produced by reacting a phenol compound having the formula:

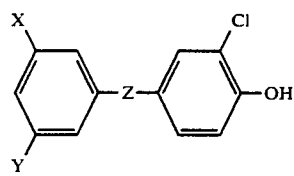

wherein X, Y and Z are each as defined above, with a compound having the formula:

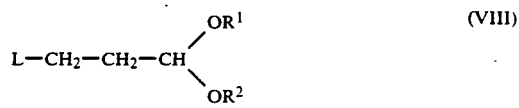

wherein $R^1$ and $R^2$ are each as defined above and L is a halogen atom, a mesyloxy group and a tosyloxy group by the known method as described in Tetrahedron Lett. 21 (1973), etc.

The 3-(4-substituted-2-chlorophenoxy)propionaldoxime ethyl ether compound (I) is also produced directly by reacting the acetal compound (VI) with ethoxyamine.

The phenol compound (VII) is produced by reacting the corresponding non-chlorinated compound, i.e. a phenol compound, having the formula:

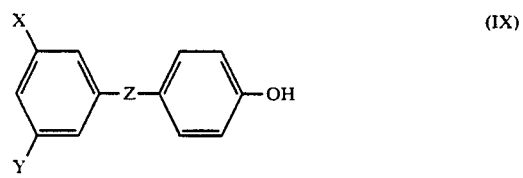

wherein X, Y and Z are each as defined above, with a chlorinating agent by the known method as described in J. Amer. Chem. Soc., 73, 2723 (1951), J. Org. Chem., 39, 1160 (1974), etc.

The molar proportion of the phenol compound IX) and the chlorinating agent is not limitative but it is ordinary to use the chlorinating agent in an amount equivalent to the phenol compound IX) or somewhat in excess. Examples of the chlorinating agent are chlorine, tert-butyl hypochlorite, sulfuryl chloride, etc. If necessary and desired, the reaction can be carried out in the presence of an inert solvent. Examples of the solvent are dichloromethane, 1,2-dichloroethane, carbon tetrachloride, benzene, acetic acid, etc. The chlorinating agent itself may be available as a reaction medium when it is liquid. The reaction temperature is usually from about −80° C. to the refluxing temperature of the reaction system, preferably from about −20° C. to the refluxing temperature of the reaction system.

The aldoxime compound (III) is prepared by reacting the aldehyde compound (II) with ethoxyamine by the known method as described in Chem. Ber., 40, 1676 (1907), etc.

After completion of the reaction, post-treatment may follow in a per se conventional manner such as extraction with an organic solvent and concentration. When necessary or desired, the product may further be purified by chromatogtaphy, distillation, recrystallization, etc.

Examples of the insect pests against which the 3-(4-substituted-2-chlorophenoxy)propionaldoxime ethyl ether compounds (I) of the invention exhibit controlling effects are as shown below.

Hemiptera

Planthoppers such as brown planthopper (*Nilaparvata lugens*), white-backed rice planthopper (*Sogatella furcifera*) and small brown planthopper (*Laodelphax striatellus*); leafhoppers such as green rice leafhopper (*Nephotettix cincticeps*), *Nephotettix virescense, Nephotettix nigropictus,*zig-zag rice leafhopper (*Recilia dorsalis*), tea green leafhopper (*Empoasca onukii*) and grape leafhopper (*Arboridia apicalis*); aphids such as cotton aphid (*Aphis gossypii*) and green peach aphrd (*Myzus persicae*); bugs; whiteflies (Aleyrodidae) such as sweet potato whitefly (*Bemisia tabaci*) and greenhouse whitefly (*Trialeurodes vaporariorum*); scales; mealy bugs; lace bugs (Tingidae); psyllids (Psyllidae), etc.

Lepidoptera

Pyralid moths (Pyralidae) such as rice stem borer (*Chilo suppressalis*), rice leafroller (*Cnaphalocrocis medinalis*) and Indian meal moth (*Plodia interpunctella*); Noctuidae such as tobacco curworm (*Spodoptera litura*), rice armyworm (*Pseudaletia separate*), cabbage armyworm (*Mamestra brassicae*) and beet semi-looper (*Autographa nigrisigna*); *Agrothis* spp. such as turnip cutworm (*Agrothis segetum*) and black cutworm (*Agrothis ipsilon*); *Heliothis* spp.; Pieridae such as common cabbageworm (*Pieris rapae crucivora*); tortricid moths (Tortricidae) such as *Adoxophyes* spp. and *Grapholita* spp.; Carposinidae such as lyonetiid moths (Lyonetiidae), leafblotch miners (Gracillariidae), gelechiid moths (Gelechiidae) and tussock moths (Lymantriidae); diamondback moth (*Plutella xylostella*), clothes moths (Tineidae), casemaking clothes moth (*Tinea translucens*) and webbing clothes moth (*Tineola bisselliella*), etc.

Diptera

Mosquitos (Calicidae) such as common mosquito (*Culex pipiens pallens*) and *Culex tritaeniorhynchus*; *Aedes* spp. such as *Aedes aegypti* and *Aedes albopictus*; Anopheles spp. such as *Anopheles sinensis*; midges (Chironomidae); Muscidae such as housefly (*musca domestica*) and false stablefly (*Muscina stabulans*); Calliphoridae; Sarcophagrdae; lesser housefly (*Fannia canicularis*); anthomyiid flies (Anthomyiidae) such as seedcorn maggot (*Delia platura*) and onion maggot (*Delia antique*); fruit flies (Tephritidae); shore flies (Ephydridae); small fruit flies (Drosophilidae); moth flies (Psychodidae); black flies (Simuliidae); Tabanidae; stable flies (Stomoxyidae) etc.

Coleoptera

Leaf beetles (Chrysomelidae) such as cucurbit beetle (*Aulacophora femoralis*), striped flea beetles (*Phyllotrata striolata*), western corn rootworm (*Diabrotica virgifora*) and southern corn root worm (*Diabrotica undecimpunctata*); scarabs (Scarabaeidae) such as cupreous chafer (*Anomala cuprea*) and soybeen beetle (*Anomala rufocuprea*); weevils (Cureulionidae) such as maize weevil (*Sitophilus zeamais*), rice water weevil (*Lissorhoptrus oryzophilus*) and adzuki bean weevil (*Callosobruchys chineneis*), etc.; darkling beetles (Tenebrionidae) such as yellow mealworm (*Tenebrio moliter*) and red flour beetles (*Tribolium castaneum*); Anobiidae; Coccinellidae such as twenty-eight-spotted ladybirds (*Epilachna vigintioctopunctata*); powderpost beetles (Lyctidae); false powderpost beetles (Bostrychidae); Cerambysidae, etc.

Dictyoptera

Blattellidae such as German cockroach (*Blattella germanica*); Blattrdae such as smokybrown cockroach (*Periplaneta fuliginosa*), American cockroach (*Periplaneta americana*), brown cockroach (*Periplaneta brunnea*) and oriental cockroach (*Blatta orientalis*), etc.

Thysanoptera

Thrips such as *Thrips palmi*, yellow tea thrips (*Scirtothrips dorsalis*) and flower thrips (*Thrips hawaiiensis*), etc.

Hymenoptera

Ants (Formicidae); sawflies (Tenthredinidae) such as cabbage sawfly (*Athalia rosae ruficornis*), etc.

Orthoptera

Mole crickets (Gryllotalpidae); grasshoppers (Acrididae), etc.

Aphaniptera

*Purex irritans*, etc.

Anoplura

*Pediculus humanus capitis, Phthirus pubis*, etc.

Isoptera

*Reticulitermes speratus, Formosan subterrauean* termite (*Coptotermes formosanus*), etc.

Among the insect pests as above exemplified, the 3-(4-substituted-2-chlorophenoxy)propionaldoxime ethyl ether compounds (I) are particularly effective in controlling those belonging to Hemiptera and also exhibit a remarkable controlling effect on planthoppers and leafhoppers in a field of rice plant.

The 3-(4-substituted-2-chlorophenoxy)propionaldoxime ethyl ether compounds (I) may be used alone as insecticides or in mixtures with other insecticides and-/or acaricides to enhance or expand their insecticidal or pesticidal use.

Examples of the other insecticides and/or acaricide include organophosphorus compounds (e.g. fenitrothion (O,O-dimethyl O-(3-methyl-4-nitrophenyl)phosphorothioate), fenthion (O,O-dimethyl O-[3-methyl-4-(methylthio)phenyl]-phosphorothioate), diazinon (O,O-diethyl-O-(2-isopropyl-6-methyl-pyrimidin-4-yl)phosphorothioate), chlorpyrifos (O,O-diethyl-O-(3,5,6-trichloro-2-pyridyl)phosphorothioate), acephate (O,S-dimethyl acetylphosphoramidothioate), methidathion (S-2,3-dihydro-5-methoxy-2-oxo-1,3,4-thiadiazol3-ylmethyl O,O-dimethylphosphorodithioate), disulfoton (O,O-diethyl S-2-ethylthioethyl phosphorothioate), DDVP (2,2-dichlorovinyldimethylphosphate), sulprofos (O-ethyl O-4-(methylthio)phenyl S-propyl phosphorodithioate), cyanophos (O-4-cyanophenyl O,O-dimethyl phosphorothioate), dioxabenzofos (2-methoxy-4H-1,3,2-benzodioxaphosphinine-2-sulphide), dimethoate (O,O-diethyl-S-(N-methylcarbamoylmethyl)dithiophosphate), phenthoate (ethyl 2-dimethoxyphosphinothioylthio(phenyl)acetate), malathion (diethyl (dimethoxyphosphinothioylthio)succinate), trichlorfon (dimethyl 2,2,2-trichloro-1-hydroxyethylphosphonate), azinphos-methyl (S-3,4-dihydro-4-oxo-1,2,3-benzotriazin-3-ylmethyl O,O-dimethylphosphoro-dithioate) and monocrotophos (dimethyl (E)-1-methyl-2-(methylcarbamoyl)vinyl phosphate), etc.); carbamate derivatives (e.g. BPMC (2-sec-butylphenyl methylcarbamate), benturacarb (ethyl N-[2,3-dihydro-2,2-dimethylbenzofuran-7-yloxycarbonyl(methyl)aminothio]-N-iso-propyl -beta-alaninate), propoxur (2-isopropoxyphenyl N-methylcarbamate), carbosulfan (2,3-dihydro-2,2-dimethyl-7-benzo[b]furanyl N-methylcarbamate), carbaryl (1-naphthyl-N-methylcarbamate), methomyl (S-methyl-N-[(methylcarbamoyl)oxy]thioacetimidate), ethiofencarb (2-(ethylthiomethyl)phenyl methylcarbamate), aldicarb (2-methyl-2-(methylthio)propionaldehyde O-methylcarbamoyloxime) and Oxamyl (N,N-dimethyl-2-methylcarbamoyloxyimino-2- (methylthio)acetamide), etc.); pyrethroides (e.g. ethofenprop (2-(4-ethoxyphenyl-2-methylpropyl-3-phenoxybenzylether), fenvalerate ((RS)-alpha-cyano-3-phenoxybenzyl (RS)-2-(4-chlorophenyl)-3-methylbutyrate), esfenvalerate ((S)-alpha-cyano-3-phenoxybenzyl (S)-2-(4-chlorophenyl)-3-methylbutyrate), ±enpropathrin ((RS)-alpha-cyano-3-phenoxybenzyl 2,2,3,3-tetramethylcyclopropanecarboxylate), cypermethrin ((RS)-alpha-cyano-3-phenoxybenzyl (1RS,3RS)- (1RS,3RS)-3-(2,2-dichlorovinyl)-2,2-d imethylcyclopropanecarboxylate), permethrin (3-phenoxybenzyl (1RS,3RS)-(1RS,3RS)-3-(2,2-dichlorovinyl)-2,2-dimethylcyclopropanec arboxylate), cyhalothrin ((R,S)-alpha-cyano-3-phenoxybenzyl (Z)-(1RS,3RS)-3-(2-chloro-3,3,3-trifluoropropenyl)-2,2-dimethylcyclopropanecarboxylate), deltamethrin ((S)-alphacyano-m-phenoxybenzyl (1R,3R)-3-(2,2-dibromovinyl)-2-dimethylcyclopropanecarboxylate) and cycloprothrin ((RS)-alpha-cyano-3-phenoxybenzyl (RS)-2,2-dichloro-1- (4-ethoxyphenyl)cyclopropanecarboxylate), etc.); thiadiazine derivatives (e.g. buprofezin (2-tert-butylimino-3-isopropyl-5-phenyl-1,3,5-triadiazin-4-one). etc.); nitroimidazolidine derivatives (e.g. imidacloprid (1-(6-chloro-3-pyridylmethyl)-N-nitro-imidazolidin-2-ylideneamine), etc.); nereistoxin derivatives (e.g. cartap (S,S'-(2-dimethylaminotrimethylene) bis(thiocarbamate), thiocyclam (N,N-dimethyl-1,2,3-trithian5-ylamine) and bensultap (S,S'-2-dimethylaminotrimethylene di(benzenethiosulphonate), etc.); halogenated hydrocarbons (e.g. endosulfan (6,7,8,9,10,10-hexachloro-1,5,5a,6,9,9a-hexahydro-6,9-methano-2,4,3-benzodioxathiepin-3-ox ide) and gamma-BHC (1,2,3,4,5,6-hexachlorocyclohexane), etc.); benzoylphenylurea derivatives (e.g. chlorfluazuron (1-[3,5-dichloro-4-(3-chloro-5-trifluoromethylpyridin-2-yloxy)phehyl]3-(2,6-difluorobenzoyl)urea), teflubenzuron (1-(3,5-dichloro-2,4-diiluorophenyl)-3-(2,6-difluorobenzoyl)urea) and flufenoxuron (1-[4-(2-chloro-4-trifluoromethylphenoxy)-2-fluorophenyl]-3-(2,6-difluorobenzoyl )urea, etc.); formamidine derivatives (e.g. amitraz (N,N'-[(methylimino)dimethylidyne]-di-2,4-xylidine) and chlordimeform (N'-(4-chloro-2-methylphenyl)-N,N-dimethylmethanimidamide), etc.).

On the practical use of the 3-(4-substituted-2-chlorophenoxy)propionaldoxime ethyl ether compounds (I) as insecticides, they may be employed as such but are normally mixed with appropriate additives such as solid carriers, liquid carriers, gaseous carriers, feed, etc. to formulate their compositions. When desired or necessary, surfactants and other adjuvants may be further incorporated therein. The compositions may be prepared into any conventional forms such as oil sprays, emulsifiable concentrates, wettable powders, flowable concentrates (e.g. water-based suspension formulations, water-based emulsion formulations), granules, dusts, aerosals, heating smoking formulations (e.g. self-burning-type smoking formulations, chemical reaction-type smoking formulations, porous ceramic plate-type smoking formulations), ULV formulations, poison baits, etc.

The composition of the invention contains generally the 3-(4-substituted-2-chlorophenoxy)propionaldoxime ethyl ether compound(s) (I) as the active ingredient in an amount of from about 0.001 % to 95 % by weight based on the composition.

Examples of the solid carrier usable for making the composition are fine powders or granules of clays (e.g. kaolin clay, diatomaceous earth, synthetic hydrated silica, bentonite, Fubasami clay, terra alba), talc, ceramics, other inorganic minerals (e.g. sericite, quartz, sulfur, activated carbon, calcium carbonate, hydrated silica), chemical fertilizers (e.g. ammonium sulfate, ammonium phosphate, ammonium nitrate, urea, ammonium chloride), etc. Examples of the liquid carrier include water, alcohols (e.g. methanol, ethanol), ketones (e.g. acetone, methyl ethyl ketone), aromatic hydrocarbons (e.g. benzene, toluene, xylene, ethylbenzene, methylnaphthalene), aliphatic hydrocarbons (e.g. hexane, cyclohexane, kerosene, gas oil), esters (e.g. ethyl acetate, butyl acetate), nitriles (e.g. acetonitriles, isobutyronitrile), ethers (e.g. diisopropyl ether, dioxane), acid amides (e.g. N,N-dimethylformamide, N,N-dimethylacetamide), halogenated hydrocarbons (e.g. dichloromethane, trichloroethane, carbon tetrachloride), dimethylsulfoxide, vegetable oils (e.g. soybean oil, cotton seed oil), etc. Examples of the gaseous carrier, i.e. a propellant, include treon gas, butane gas, LPG (liquefied petroleum gas), dimethyl ether, carbon dioxide, etc.

Examples of the surfactant are alkylsulfates, alkylsultonates, alkylarylsultonates, alkyl aryl ethers and polyoxyethylene derivatives thereof, polyethylene glycol ethers, polyvalent alcohol esters, sugar alcohol derivatives, etc. Examples of the adjuvants such as binders and dispersing agents are casein, gelatin, polysaccharides (e.g. starch powders, gum arabic, cellulose derivatives, alginic acid), lignin derivatives, bentonite, sugars, synthetic water-soluble high molecular weight substances e.g. polyacrylic alcohol, polyvinylpyrrolidone, polyacrylic acid), etc. Examples of the stabrlizer include PAP (acidic isopropyl phosphate), BHT (2,6-di-tert-butyl-4-methylphenol), BHA (mixture of 2-tert-butyl-4-methoxyphenol and 3-tert-butyl-4-methoxyphenol), vegetable oils, mineral oils, surfactants, fatty acids or esters thereof, etc.

The base material for self-burning-type smoking formulations may include, for example, burning heat-generating agents such as nitrates, nitrites, guanidine salts, potassium chlorate, nitrocellulose, ethyl cellulose and wood powders, pyrolysis-promoting agents such as alkali metal salts, alkaline earth metal salts, dichromates and chromates, oxygen-supplying agents such as potassium nitrate, burning-supporting agents such as melamine and wheat starch, extenders such as diatomaceous earth, binders such as synthetic pastes, etc. The base material for chemical reation-type smoking formulations can include, for example, heat-generating agents such as alkali metal sulfides, alkali metal polysulfides, alkali metal hydrosulfides, hydrated salts of alkali metals and calcium oxide, catalyzing agents such as carbonaceous substances, iron carbide and activated clay, organic foaming agents such as azodicarbonamide, benzenesulfonyl hydrazides, dinitrosopentamethylenetetramine, polystyrene and polyurethane, fillers such as natural fiber pieces and synthetic fiber pieces, etc. The base material for poison baits may contain feed components such as crop powders, essential vegetable oil, sugars and crystalline cellulose, antioxidants such as dibutylhydroxyrtolune and nordihydroguaiaretic acid, preservatives such as dehydroacetic acid, feeding error preventing agnets such as red paper powders, incentive flavors such as cheese flavor and onion flavor, etc.

Flowable concentrates (water-based suspension or emulsion formulations) are generally obtained by dispersing about 1 to 75 parts by weight of the 3-(4-substituted-2-chlorophenoxy)propionaldoxime ethyl ether compound (I) as the active ingredient finely and uniformly into water containing about 0.5 to 15 parts by weight of a dipersing agent, about 0.1 to 10 parts by weight of a suspending agent (e.g. protective colloids, compounds giving a thixotropic property) and optionally about 0 to 10 parts by weight of an auxiliary agent(s) such as a defoaming agent, an anti-corrosive agent, a stabilizing agent, a spreading agents, penetration auxiliaries, antifreezing agent, an antibacterial agent, an antimolding agent and the like. The use of an oil, into which the active ingredient is hardly soluble, in place of water affords oil-based suspension formulations. Examples of the protective colloids as above mentioned are gelatin, casein, gums, cellulose ethers, polyvinyl alcohol, etc. Examples of the compounds giving a thixotropic property are bentonite, aluminum magnesium silicate, xanthane gum, polyacrylic acid, etc.

The composition of the invention thus obtained may be used as such or after diluting with water. It may be also used in a mixture with any other active component or composition chosen from insecticides, nematocides, acaricides, fungicides, bacteriocides, herbicides, plant growth regulators, synergistic agents, fertilizers, soil conditioners, animal feed, etc. Alternatively, the composition of the invention may be applied separately but simultaneously with said other active component or composition.

For the purpose of controlling insect pests in the agricultural field, the 3-(4-substituted-2-chlorophenoxy)propionaldoxime ethyl ether compound (I) according to the present invention may be applied to the insect pests or the locus where the insect pests propagate generally in an amount of about 0.001 g to 500 g, and preferably about 0.1 g to 500 g per 10 ares. when the 3-(4-substituted-2-chlorophenoxy)propionaldoxime ethyl ether compound (I) is applied in a form of emulsifiable concentrate, wettable powder, flowable concentrate or the like after dilution with water, its concentration may be from about 0.0001 to 1000 ppm. Granules, dusts, etc. may be used as such, i.e. without water dilution. When the 3-(4-substituted-2-chlorophenoxy) propionaldoxime ethyl ether compound (I) is used for household or public hygiene, it may be used in the form of emulsifiable concentrate, wettable powder, flowable concentrate or the like with water dilution, etc. In this case, the concentration of the active ingredient may be from about 0.0001 to 10,000 ppm. In case of oils, aerosol, ±umigants, ULV formulations, poison baits, etc., they may be applied as such. However, the doses and concentrations may vary within broad ranges depending upon the composition, the application time, the place applied, the application method, the kind of insect pests, the condition of damage, etc. and may be increased or decreased, irrespective of the general ranges set forth above.

Practical and presently preferred embodiments of the invention will be hereinafter explained in more detail referring to Production Examples, Formulation Examples and Test Examples. These examples, however, should not be construed to be limitative.

In the following Production Examples, % is by weight unless otherwise indicated.

PRODUCTION EXAMPLE 1

Production of 3-[2-chloro-4-(3,5-difluorophenoxy)phenoxy)]propionaldoxime ethyl ether by Process A To a solution of 0.5 g of 3-[2-chloro-4-(3,5-difluorophenoxy)phenoxy]propionaldehyde in 10 ml of pyridine, there was added little by little 0.19 g of ethoxyamine hydrochloride with stirring and ice-cooling for 10 minutes. Then, the mixture was followed by stirring at room temperature overnight. The reaction mixture was poured into water and extracted with toluene. The extract was washed with water, concentrated under reduced pressure. The residue was subjected to silica gel chromatography to give 0.43 g of 3-[2-chloro-4-(3,5-difluorophenoxy)phenoxy]propionaldoxime ethyl ether (Compound No. 1) as a colorless oily substance.

Yield, 75 %. $n^{26.1}{}_D 1.5385$.

PRODUCTION EXAMPLE 2

Production of 3-[2-chloro-4-(3-fluorophenoxy)phenoxy]propionaldoxime ethyl ether by Process A To a solution of 1.0 g of 3-[2-chloro-4-(3-fluorophenoxy)phenoxy]propionaldehyde in 10 ml of pyridine, there is added little by little 0.39 g of ethoxyamine hydrochloride with stirring and ice-cooling for 10 minutes. Then the mixture is followed by stirring at room temperature overnight. The reaction mixture is poured into water and extracted with toluene. The extract is washed with water, concentrated under reduced pressure. The residue is subjected to silica gel chromatography to give 3-[2-chloro-4-(3-fluorophenoxy)phenoxy]propionaldoxime ethyl ether (Compound No. 2).

PRODUCTION EXAMPLE 3

Production of 3-(2-chloro-4-benzylphenoxy)propionaldoxime ethyl ether by Process A To a solution of 1.0 g of 3-(2-chloro-4-benzylphenoxy)propionaldehyde in 10 ml of pyridine, there was added dropwise 0.43 g of ethoxyamine hydrochloride with stirring and ice-cooling for 10 minutes. Then the mixture was followed by stirring at room temperature overnight. The reaction mixture was poured into water and extracted with toluene. The extract was washed with water, concentrated under reduced pressure. The residue was subjected to silica gel chromatography to give 0.79 g of 3-(2-chloro-4-benzylphenoxy)propionaldoxime ethyl ether (Compound No. 3) as a colorless oily substance.

Yield, 68 %. $n^{24.4}{}_D 1.5620$.

PRODUCTION EXAMPLE 4

Production of 3-[2-chloro4-(3,5-difluorobenzyl)phenoxy]propionaldoxime ethyl ether by Process A To a slution of 1.0 g of 3-[2-chloro-4-(3,5-difluorobenzyl)phenoxy]propionaldehyde in 10 ml of pyridine, there was added little by little 0.38 g of ethoxyamine hydrochloride with stirring and ice-cooling for 10 minutes. Then, the mixture was followed by stirring at room temperature overnight. The reaction mixture was poured into water and extracted with toluene. The extract was washed with water, concentrated under reduced pressure. The residue was subjected to silica gel chromatography to give 0.80 g of 3-[2-chloro-4-(3,5-difluorobenzyl)phenoxy]propionaldoxime ethyl ether (Compound No. 4) as a colorless oily substance.

Yield, 70 %. $n^{24.4}{}_D$ 1.5398

PRODUCTION EXAMPLE 5

Production of Compound No. 1 by Process B

To a solution of 1.0 g of 3-[2-chloro-4-(3,5-difluorophenoxy)phenoxy]propionaldoxime in 20 ml of N,N-dimethylformamide, there was added 0.15 g of sodium hydride (60% dispersion in mineral oil) with stirring and ice-cooling. After 2 hours, 0.59 g of ethyl iodide was added dropwise to the resultant mixture and then the mixture was stirred at room temperatur overnight. After the reaction was completed, the reaction mixture was poured into water, extracted with toluene. The extract was washed with water, concentrated under reduced pressure. The residue was subjected to silica gel chromatography to give 0.71 g of Compound No. 1 as a colorless oily substance. Yield, 65 %.

PRODUCTION EXAMPLE 6

Production of Compound No. 3 by Process B

To a slution of 1.0 g of 3-[2-chloro-4-benzylphenoxy)phenoxy]propionaldoxime in 20 ml of N,N-dimethylformamide, there was added 0.15 g of sodium hydride (60% dispersion in mineral oil) with stirring and ice-cooling. After 2 hours, 0.59 g of ethyl iodide was added dropwise to the resultant mixture and then the mixture was stirred at room temperature overnight. After the reaction was completed, the reaction mixture was poured into water, extracted with toluene. The extract was washed with water, concentrated under reduced pressure. The residue was subjected to silica gel chromatography to give 0.61 g of Compound No. 3 as a colorless oily substance. Yield, 56 %.

PRODUCTION EXAMPLE 7

Production of 3-[2-chloro-4-(3-fluorobenzyl)phenoxy]propionaldoxime ethyl ether by Process B To a solution of 1.0 g of 3-[2-chloro-4-(3-fluorobenzyl)phenoxy]propionaldoxim in 20 ml of N,N-dimethylformamide, there was added 0.14 g of sodium hydride (60% dispersion in mineral oil) with stirring and ice-cooling. After 2 hours, 0.56 g of ethyl iodide was added dropwise to the resultant mixture and then the mixture was stirred at room temperature overnight. After the reaction was completed, the reaction mixture was poured into water, extracted with toluene. The extract was washed with water, concentrated under reduced pressure. The residue was subjected to silica gel chromatography to give 0.65 g of 3-[2-chloro-4-(3-fluorobenzyl)phenoxy]propionaldoxime ethyl ether (Compound No. 5) as a colorless oily substance.

Yield, 60 %. $n^{23.4}{}_D$ 1.5507.

In Formulation Examples as set forth below, parts and % are all by weight. The compound numbers correspond to those as described above.

FORMULATION EXAMPLE 1

Emulsifiable Concentrate

To a solution of 10 parts of each of Compounds Nos. 1 to 5 in 35 parts of xylene and 35 parts of dimethylformamide, 14 parts of polyoxyethylene styrylphenyl ether and 6 parts of calcium dodecylbenzenesulfonate are added, and the resultant mixture is thoroughly mixed while stirring to give an emulsifiable concentrate containing the active ingredient in 10 %.

FORMULATION EXAMPLE 2

Wettable Powder

Twenty parts of each of Compounds Nos. 1 to 5 are added to a mixture of 4 parts of sodium laurylsulfate, 2 parts of calcium ligninsulfonate, 20 parts of fine powders of synthetic hydrated silica and 54 parts of diatomaceous earth, and the resultant mixture is stirred in a mixer to give a wettable powder containing the active ingredient in 20 %.

FORMULATION EXAMPLE 3

Granules

Five parts of sodium dodecylbenzenesulfonate, 30 parts of bentonite and 60 parts of clay are added to 5 parts of each of Compound Nos. 1, 3, 4 and 5, and the resultant mixture is pulverized and kneaded with a suitable amount of water. The mixture is granulated in a granulator and air-dried to give granules containing the active ingredient in 5 %.

FORMULATION EXAMPLE 4

Dusts

To a mixture of 1 part of fine powders of synthetic hydrated silica, 1 part of an aggregating agent "Driless B" manufactured by Sankyo Co., Ltd.) and 7.7 parts of clay, 0.3 part of each of Compound Nos. 1, 3, 4 and 5 is added, the resultant mixture is well pestled in a mortar and further stirred in a mixer. To the thus obtained mixture, there are added 90 parts of cut clay, followed by mixing to give dusts containing the active ingredient in 0.3 %.

FORMULATION EXAMPLE 5

Dusts

A mixture of 0.3 part of each of Compound Nos. 1, 3, 4 and 5, 2 parts of fenitrothion (O,O-dimethyl O-(3-methyl-4-nitrophenyl)phosphorothioate as an organophosphorus insecticide, 3 parts of fine powders of synthetic hydrated silica, 1 part of "Driless B" and 3.7 parts of clay are pestled in a mortar and stirred in a mixer. Then, 90 parts of cut clay are added thereto, and the resultant mixture is further mixed in a sack to give dusts.

FORMULATION EXAMPLE 6

Dusts

A mixture of 0.3 part of each of Compound Nos. 1, 3, 4 and 5, 2 parts of BPMC (O,O-sec-butylphenyl N-methylcarbamate) as a carbamate insecticide, 3 parts of fine powders of synthetic hydrated silica, 1 part of "Driless B" and 3.7 parts of clay are pestled in a mortar and stirred in a mixer. Then, 90 parts of cut clay are added thereto, and the resultant mixture is further mixed in a sack to give dusts.

FORMULATION EXAMPLE 7

Dusts

To a solution of 1 part of each of Compound Nos. 1 to 5 in an appropriate amount of acetone, 5 parts of fine powders of synthetic hydrated silica, 0.3 part of PAP (acidic isopropyl phosphate) and 93.7 parts of clay are added, and the resultant mixture is stirred in a mixer, followed by evaporation of acetone to give dusts containing the active ingredient in 1 %.

FORMULATION EXAMPLE 8

Flowable Concentrate

To 40 parts of an aqueous solution containing 2 parts of polyvinyl alcohol, 10 parts of each of Compound Nos. 1, 3, 4 and 5 are added, and the resultant mixture is stirred in a mixer. To the thus obtained dispersion, 40 parts of an aqueous solution containing 0.05 part of xanthane gum and 0.1 part of aluminum magnesium silicate are added, followed by addition of 10 parts of propylene glycol. The mixture is gently stirred to give a flowable concentrate containing the active ingredient in 10 %.

FORMULATION EXAMPLE 9

Oil Spray

Into a mixture of 5 parts of xylene and 5 parts of trichloroethane, 0.1 part of each of Compound Nos. 1 to 5 is dissolved, and the resultant solution is mixed with 89.9 parts of deodorized kerosene to give an oil spray containing the active ingredient in 0.1 %.

FORMULATION EXAMPLE 10

Oil-based Aerosol

A solution of 0.1 part of each of Compound Nos. 1 to 5, 0.2 part of tetramethrin (2,2-dimethyl-3-(2-methyl-1-propenyl)cyclopropanecarboxylic acid (1,2,3,4,5,7-hexahydro-1,3-dioxo-2H-isoindol-2-yl)methyl ester) and 0.1 part of d-phenothrin (2,2-dimethyl-3-(2-methyl-1-propenyl)cyclopropanecarboxylic acid (3-phenoxyphenyl)methyl ester) in a mixture of 10 parts of trichloroethane and 59.6 parts of deodorized kerosene is filled in an aerosol container. After provision of a valve, 30 parts of a propellant (liquefied petroleum gas) is filled through the valve under compression to give an oil-based aerosol.

FORMULATION EXAMPLE 11

Water-based Aerosol

A solution of 0.2 part of each of Compound Nos. 1 to 5, 0.2 part of d-allethrin ((2,2-dimethyl-3-(2-methyl-1-propenyl)cyclopropanecarboxylic acid 2-methyl-4-oxo-3-(2-propenyl)-2-cyclopenten-2-yl ester), 0.2 part of d-phenothrin, 5 parts of xylene. 3.4 parts of deodorized kerosene and 1 part of an emulsifier ("ATMOS 300" ®, Atlas Chemical Co., Ltd.) in 50 parts of distilled water is filled in an aerosol container. After provision of a valve, 40 parts of a propellant (liquefied petroleum gas) is filled through the valve under compression to give a water-based aerosol.

FORMULATION EXAMPLE 12

Fumigant

Each of Compound Nos. 1 to 5 (100 mg) is dissolved in an appropriate amount of acetone, and the resultant solution is impregnated with a porous ceramic plate (4.0×4.0×1.2 cm) t o give a fumigant.

The following Test Examples show some of test results which support the controlling effect of the 3-(4-substituted-2-chlorophenoxy)propionaldxime ethyl ether compounds (I) on insect pests. The compound numbers correspond to those as described above. The compounds used for comparison are as follows:

| Compound symbol | Chemical structure | Remarks |
|---|---|---|
| A | ⟨phenyl⟩—O—⟨phenyl⟩—OCH$_2$—CH$_2$CH=NO—C$_2$H$_5$ | Compound disclosed in J.P.-A60-56948 |

TEST EXAMPLE 1

Metamorphosis inhibitory activity against brown rice planthopper nymphs

An emulsifiable concentrate prepared according to Formulation Example 1 was diluted with water to make a predetermined concentration. The dilution was sprayed onto rice plants cultivated in polyethylene cups at a rate of 20 ml/2 pots on a turning table. After air-drying, the plants were infested with about ten 3rd instar nymphs of brown rice planthopper (*Nilaparvata lugens*). After 10 days, the number of normal adults was counted to obtain an emergence inhibitory rate. As the results, Compound Nos. 1, 3, 4 and 5 showed a 100 % emergence inhibition at a concentration of 5 ppm and 0.5 ppm. On the other hand, Compound A showed only a 5 % emergence inhibition at a concentration of 5 ppm.

TEST EXAMPLE 2

Reproduction inhibitory activity against green rice leafhopper

An emulsifiable concentrate prepared according to Formulation Example 1 was diluted with water to make a predetermined concentration. The dilution was sprayed onto rice plants (about 20 cm in height) cultivated in plastic pots (1/5000 are in width) at a rate of 40 ml/2 pots on a turning table. After air-drying, the pots were covered with wire cages, and each 10 male and female adults of green rice leafhopper (*Nephotettix cincticeps*) were released in each of the cages. After 3 weeks, the number of nymphs was counted to obtain a reproduction rnhibitory rate. The results showed that Compound Nos. 1 and 4 had an effect of a 100 % reproduction inhibition at a concentration of 100 ppm.

TEST EXAMPLE 3

Reproduction inhibitory activity against brown rice planthopper

An emulsifiable concentrate prepared according to Formulation Example 1 was diluted with water to make a predetermined concentration. The dilution was sprayed onto rice plants (about 20 cm in height) cultivated in plastic pots (1/5000 are in width) at a rate of 40 ml/2 pots on a turning table. After air-drying, the pots were covered with wire cages, and each 5 male and female adults of brown rice planthopper (*Nilaparvata lugens*) were released in each of the cages. After about 3 weeks, the number of nymphs was counted to obtain a reproduction inhibitory rate. The results showed that Compound Nos. 1, 3, 4 and 5 had an effect of a 100 % reproductuion inhibition at a concentration of 100 ppm. On the other hand, Compound A didn't show an emergence inhibition at a concentration of 100 ppm at all.

What is claimed is:

1. A 3-(4-substituted-2-chlorophenoxy)propionaldoxime ethyl ether compound of the formula:

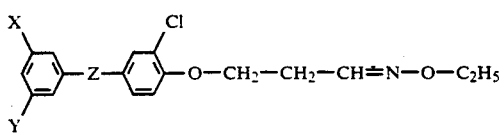

wherein X and Y are, the same or different, a hydrogen atom or a fluorine atom; Z is an oxygen atom or a methylene group in the proviso that X and Y are not a hydrogen atom at the same time when Z is an oxygen atom.

2. The 3-(4-subtituted-2-chlorophenoxy) propionaldoxime ethyl ether compound which is 3-[2-chloro-4-(3,5-difluorophenoxy)phenoxy]propionaldoxime ethyl ether.

3. The 3-(4-substituted-2-chlorophenoxy) propionaldoxime ethyl ether compound which is 3-[2-chloro-4-(3-fluorophenoxy)phenoxy]propionaldoxime ethyl ether.

4. The 3-(4-substituted-2-chlorophenoxy) propionaldoxime ethyl ether compound which is 3-(2-chloro-4-benzylphenoxy)propionaldoxime ethyl ether.

5. The 3-(4-substituted-2-chlorophenoxy) propionaldoxime ethyl ether compound which is 3-[2-chloro-4-(3,5-difluorobenzyl)phenoxy]propionaldoxime ethyl ether.

6. The 3-(4-substituted-2-chlorophenoxy) propionaldoxime ethyl ether compound which is 3-[2-chloro-4-(3-fluorobenzyl)phenoxy]propionaldoxime ethyl ether.

7. A composition for controlling insect pests which comprises an effective amount of the 3-(4-substituted-2-chlorophenoxy) propionaldoxime ethyl ether compound according to claim 1 and an inert carrier.

8. A method for controlling insect pests which comprises applying an effective amount of the 3-(4-substituted-2-chlorophenoxy)propionaldoxime ethyl ether compound according to claim 1 to the insect pests or the locus where the insect pests propagate.